United States Patent [19]

Russo

[11] 4,060,074
[45] Nov. 29, 1977

[54] INHALATION DEVICE

[75] Inventor: Ronald D. Russo, Hamden, Conn.

[73] Assignee: Chesebrough-Pond's, Inc., Greenwich, Conn.

[21] Appl. No.: 657,242

[22] Filed: Feb. 11, 1976

[51] Int. Cl.² .......................................... A61M 16/00
[52] U.S. Cl. ................................. 128/2.08; 272/99 R
[58] Field of Search ............ 128/2.08, 2.05 V, 2.05 F, 128/142 R, 185, 202, 205, 145.8, 276, 277, 278; 272/99 R; 73/419, 205 R, 147; 116/117 B, 117 C, 117 R

[56] References Cited

U.S. PATENT DOCUMENTS

| 393,869 | 12/1888 | Warren | 128/201 |
|---|---|---|---|
| 515,637 | 2/1894 | Wilhide | 272/99 R |
| 793,177 | 6/1905 | Cady | 128/2.08 |
| 892,432 | 7/1908 | Judson | 272/27 |
| 1,621,354 | 3/1927 | Dawley | 73/205 R |
| 1,926,748 | 9/1933 | MacKenzie et al. | 128/2.05 R |
| 2,100,898 | 11/1937 | Bernett | 273/95 |
| 3,087,278 | 4/1963 | Waggle, Jr. | 46/44 |
| 3,695,608 | 10/1972 | Hanson | 128/2.08 |
| 3,754,546 | 8/1973 | Cooper | 272/99 R |

FOREIGN PATENT DOCUMENTS 1,112,252   8/1961   Germany ............................. 128/278

Primary Examiner—Robert W. Michell
Assistant Examiner—Henry J. Recla
Attorney, Agent, or Firm—Morgan, Finnegan, Pine, Foley & Lee

[57] ABSTRACT

An incentive inhalation device which induces respiratory exercise and which is inexpensive, safe and easy to handle and operate. The device includes a container having a plurality of flow measurement chambers which are vertical when the device is in its upright position. In each chamber is housed a flow rate indicator, such as a light-weight article and ball, that normally rests at the bottom thereof. The bottom of each chamber is open to surrounding atmosphere and the top of each chamber is open to a common passageway. In operation, the patient or user withdraws air from the common air passageway and chambers. When the patient achieves a precalibrated flow rate the indicators sequentially rise to the top of each chamber. To prevent disruption of air flow into the passageway and surprise or shock to the user, means are provided in the last chamber to prevent the indicator from closing the last chamber to the common air passageway.

15 Claims, 10 Drawing Figures

INHALATION DEVICE

FIELD OF THE INVENTION

The present invention relates to an incentive inhalation device which induces progressive expansion and use of lungs and respiratory musculature.

BACKGROUND OF THE INVENTION

It is often necessary to induce patients to expand and use their lungs and respiratory musculature. Post-surgical, bedridden, inactive, obese and geriatric patients do not utilize their respiratory systems fully. Pain, illness and feebleness inhibit use. As a consequence, these people are prone to pulmonary complications such as lung congestion and hypostatic pneumonia. The inefficient use of the respiratory system also can retard healing and cause muscle atrophy.

Thus, a need exists to provide patients with an incentive which encourages use of their respiratory systems. In general, presently available apparatus for inducing said use by inhalation is relatively expensive and awkward to handle. Further, the apparatus is comparatively costly and complex, and is generally limited to hospital use because of the complexities and costs. In addition, presently available apparatus is made up of a multiplicity of parts which, when dropped, are susceptible to breakage and which are costly to replace.

It is an object of this invention, therefore, to provide a new and improved device which induces progressive respiratory exercises through inhalation without drawbacks of presently available devices and systems.

Among the other objects of this invention is to provide an inhalation device which provides a progressive incentive and encourages use by ease of handling and operation; to provide an inhalation device which is safe to use; to provide an inhalation device, the successful use of which easily can be seen and measured by the patient, nurse or others; and to provide an inhalation device which accomplishes the foregoing while being relatively inexpensive.

Additional objects and advantages will be set forth in part hereinafter and in part will be obvious herefrom or may be learned with the practice of the invention, the same being realized and obtained by means of the respiratory stimulator recited in the appended claims.

SUMMARY OF THE INVENTION

In accordance with the invention, there is provided an inhalation device comprising a see-through container having in its upright position a plurality of vertical flow measurement chambers, each of which includes a flow rate indicator, such as a lightweight article or ball, which normally rests at the bottom or lower portion thereof. A clearance fit is provided between each indicator and its chamber wall which allows for free vertical movement of the indicator for restricts air flow about the indicator for causing it to rise when a precalibrated inhalation effort is achieved. Extending into the lower portion of each chamber is an opening which connects the chamber to the surrounding atmosphere at a point at least partially below the flow rate indicator. In the preferred embodiment the vertical chambers are in adjacent compartments and the lower openings are ports or slots which extend through the front and back walls thereof.

Extending through the top wall of each compartment is a port which connects the chamber to an air inhalation passageway. The passageway is connected to the top ports and includes an outlet to which is connected means, such as a flexible tubing and mouthpiece, which allow a person to withdraw air from each chamber.

In use, a person places his or her mouth over the mouthpiece and inhales. This causes air to flow through the lower slots, up, against and around the indicators, through the chambers and the top ports into the air passageway. When a precalibrated inhalation effort is achieved by the user, the upward air flow in the chambers causes the indicators to sequentially rise to the top of the chamber. To prevent disruption of air flow into the passageway and surprise or shock the user, means are provided in the last chamber which prevent the indicator from closing the last top port.

The device of the invention is particularly useful for inducing progressive inspiration which meet desired inhalation efforts. For example, a precalibrated amount of inhalation for a predetermined time is required to raise the indicator to the top of the chamber closest to the passageway outlet and precalibrated additional amounts of inhalation for predetermined additional times are required to sequentially raise the indicator in the other chambers. In the preferred embodiment illustrated in the drawings and disclosed hereinafter, at least 1000 cubic centimeters per second must be inspired by the user to raise the ball to the top of each chamber. Accordingly, when the desired flow rate is maintained for three seconds, all three balls will be at the top of the chambers indicating that at least 3000 cubic centimeters of air has been inspired.

Furthermore, in the preferred embodiment, the air outlet is at the bottom and front of the device, and the passageway extends over the top of the compartments and along one side of the container so that the user and others easily can see the articles or balls.

With the multi-chambered device of the invention, the user readily can see and measure progress. With increased lung use the user finds that he or she can raise a multiplicity of indicators. Thus, the device provides incentive levels of achievement for the patient which are designed to correspond to increased use of the respiratory system and to progressive restoration and maintenance of lung capacity and musculatory strength.

In construction, the device is compact and safe. Within the inhalation passageway there is provided a filter which prevents loose particles picked up in the air flow from exiting and being inhaled by the user. In addition, where the device is made of several plastic components, they are placed together and preferably are ultrasonically welded into a single integral unit. This obviates the need of deleterious materials, such as glue, which are known to give off residual vapors over a long period of time.

Moreover, it is within the scope of the invention to vary the inhalation effort required to cause the indicator in each chamber to rise to the top of the chambers. In one embodiment this is done by tilting the device, e.g., rearwardly, so that the indicators can be raised to the top of the container more easily. Particularly ill or feeble patients thereby are provided with an incentive level they can achieve, and, in so doing, obtain needed respiratory exercise. To be able to accurately measure the flow rate when the container is tilted, means, such as a platform, are provided which can maintain the container at the desired angle. For example, when the container is tilted rearwardly 65°, an inhalation rate of only 650 cubic centimeters per second must be maintained for three seconds to sequentially raise the balls to the tops of the chambers.

In addition, a dispenser, such as a nebulizer, can be placed at the outlet end of the device for inhalation of medicine upon inspiration by the patient.

BRIEF DESCRIPTION OF THE DRAWINGS

The following is a detailed description together with accompanying drawings of a preferred embodiment of the invention. It is to be understood that the invention is capable of modification and variation apparent to those skilled in the art within the spirit and scope of the invention.

In the drawings.

Figure 1:
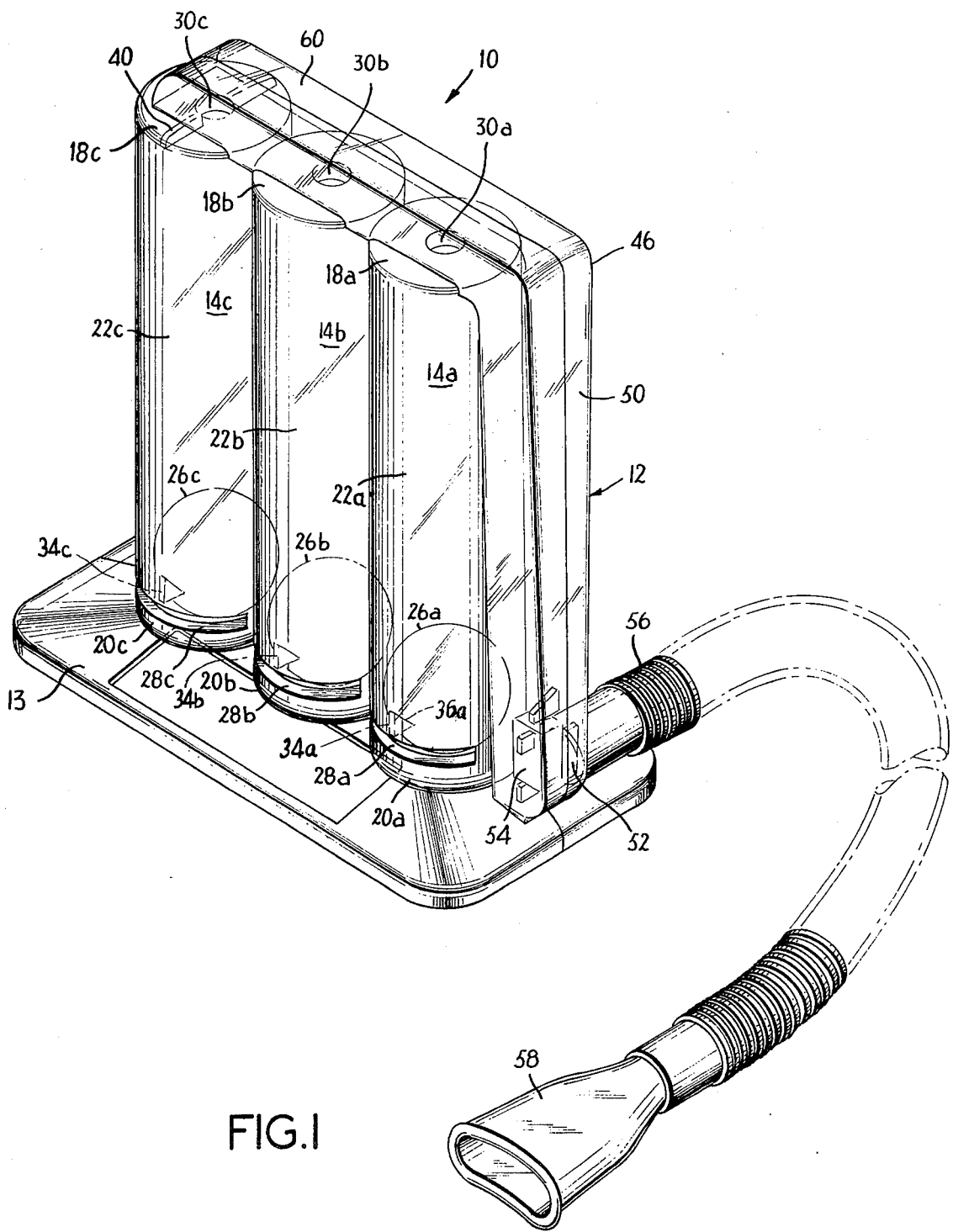
FIG. 1 is a perspective view of an inhalation device constructed in accordance with the present invention.

Referring first to FIGS. 1-4 of the drawings, the inspirator 10 is a transparent break resistant, integral unit which includes a container 12 mounted on a base 13. In the upright position the container 12 has three vertical compartments 14a, 14b, and 14c, spaced apart by the interconnecting webs 16a and 16b. The structure and function of the three compartments, 14a, 14b and 14c are identical. Accordingly, unless otherwise specified, the following description of compartment 14a applies equally to compartments 14b and 14c.

The compartment 14a has a top wall 18a, a bottom wall 20a and a transparent, vertical cylindrical wall 22a therebetween which from a vertical, flow measurement chamber 24a for a flow rate indicator, such as a plastic ball 26a.

The relative diameter of the ball 26a to the inner diameter of the cylindrical wall 22a is such that it provides for free movement of the ball 26a within the chamber 24a while providing a minimum clearance between the wall 22a and ball 26a. If the gap or clearance between the ball 26a and wall 22a is too small, the ball 26a may become stuck in the chamber 24a. If the gap is too large, the desired inhalation effort will not cause the ball 26a to rise. In the illustrated embodiment, a total gap or clearance fit of about 0.40 inches to 0.55 inches is provided between the ball 26a and inner surface of wall 22a.

Extending through and across the front and back of the lower portion of the compartment wall 22a is a rectangularly shaped slot 28a which connects the lower portion of the chamber 24a to the surrounding atmosphere. Inasmuch as the compartment wall 22a is cylindrical, slot 28a also is in the shape of an arc. The dimensions for each segment of the slot 28a are 1.250 inches in length and 0.156 inches in height.

Extending through the center of the top wall 18a is a port 30a which connects the top portion of chamber 24a with an overhead passageway, hereinafter described in detail. The breadth of the port 30a allows for the withdrawal of air from the chamber 24a which causes the ball 26a to rise while being adapted to be closed by the ball 26a when it reaches the top of the chamber 24a when the user inspires air at the desired rate. In the illustrated embodiment the port 30a has a diameter of about 0.3125 inches and the ball 26a has a diameter of about 1.00 inches.

To facilitate the rise of the ball 26a, opposing ridges 32a and 34a extend inwardly from the front and back portion of the cylindrical wall 22a immediately above the slot 28a. Each ridge 32a, 34a, is in the form of a right triangle with the hypotenuses thereof forming the upper and downwardly sloping surface 36a. The ball 26a normally rests on these downwardly sloping surfaces 36a so that only the lowermost segment of the ball 26a extends across the upper portion of the slot 28a.

To prevent a disruption of air flow by reason of the balls 26a, 26b and 26c, rising to the top of their chambers 24a, 24b and 24c, a ridge 40 is provided in the last chamber 24c which depends downwardly from the top wall 18 adjacent to the port 30c. In use, the ball 26c cannot close port 30c and interrupt the flow of air to cause surprise and shock to the user.

The supporting base 13 extends beyond the container 12 and enables the device 10 to stand by itself in a vertical upright position. As illustrated, the base 13 is rectangularly shaped and is in the form of an inverted curved disc-like structure. The container 12 is centrally positioned on the upper convex platform surface and the platform 13 itself stands on its outer perimeter.

About one side and top of the container 12 is an inverted "L" shaped channel 46 which forms an air inhalation passageway 48.

Figure 3:
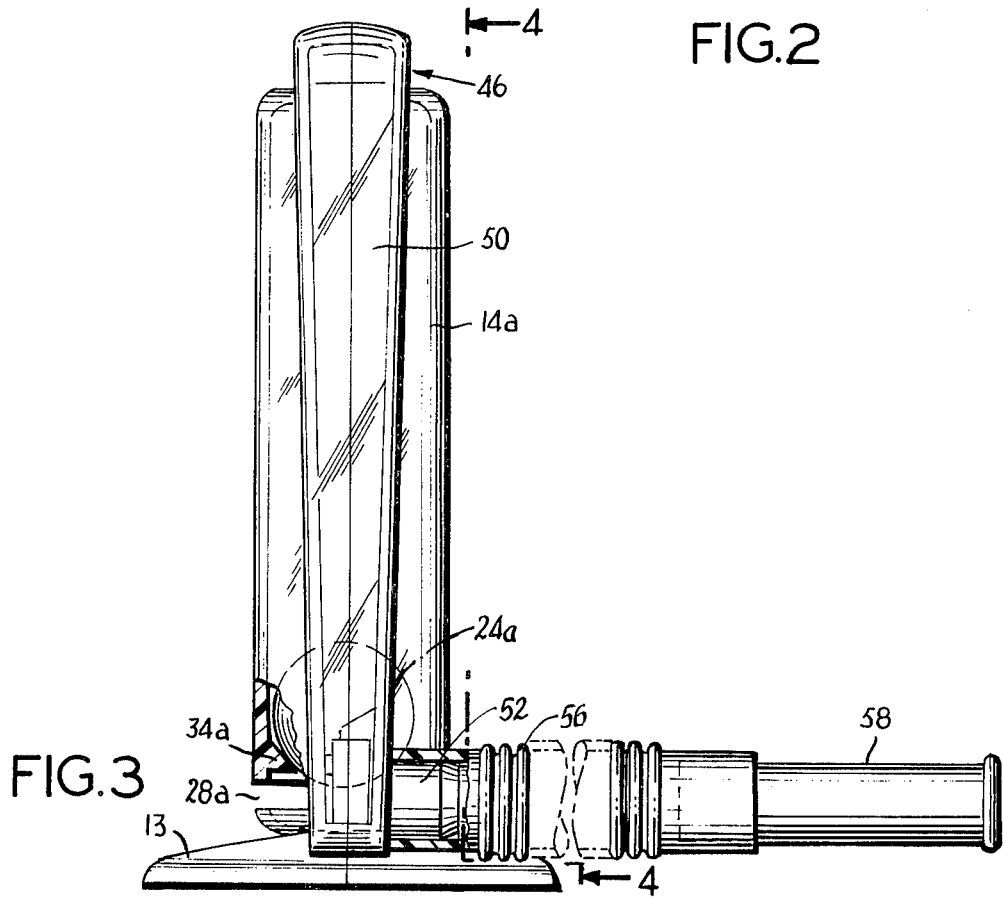
FIG. 3 is a side view of the device illustrated in FIG. 1 in which the bottom of the container is partially broken away to show details in construction.

As illustrated in FIG. 3 the vertical section 50 of the channel 46 is tapered with the narrowest segment at the bottom of the container 12 connected to a tubular outlet 52.

The outlet 52 extends horizontally and outwardly over the base 13. Forced fitted into the outlet 52 is a rectangularly shaped filter 54 which captures loose particles that may pass into the passageway upon inhalation. Slidably fitted over the outlet tube 52 is flexible accordian tubing 56 which has at its other end a mouthpiece 58 slidably fitted thereinto.

Figure 4:
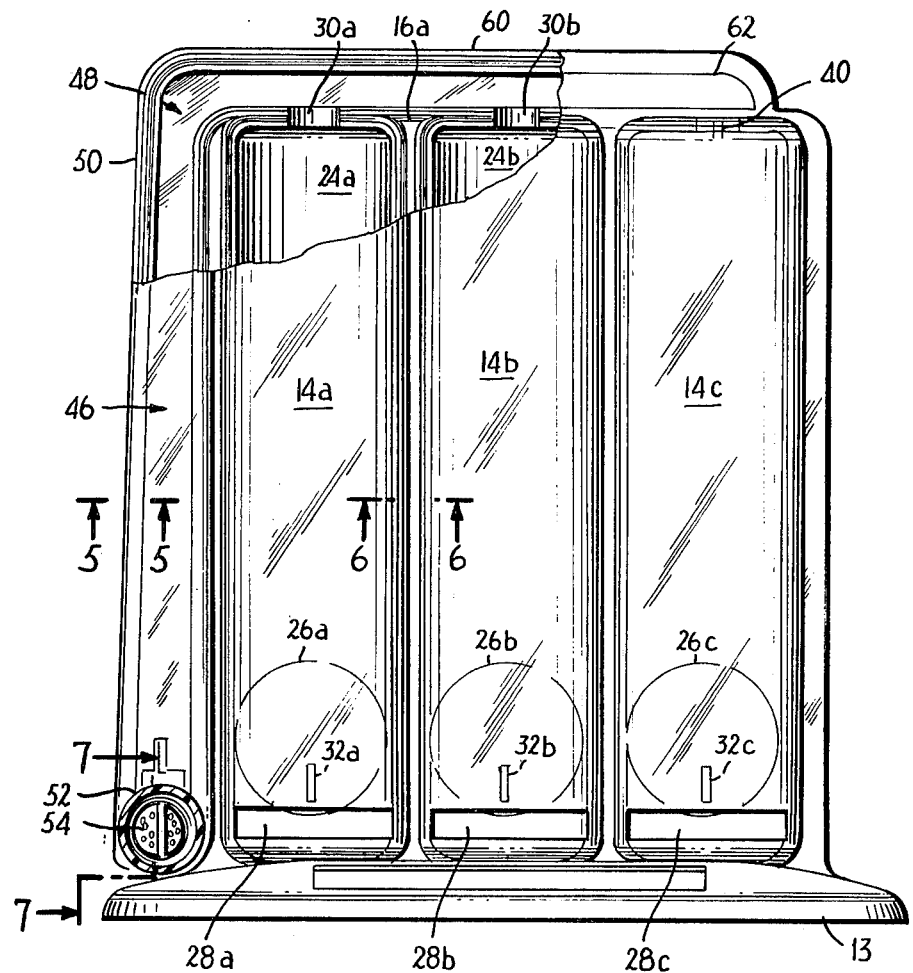
FIG. 4 is a front view of the device illustrated in FIG. 1.

As shown in FIG. 4 the horizontal section 60 of the passageway 48 extends over the central portion of the top walls 18a, and 18b and 18c of compartments 16a, 16b and 16c, opens to top ports 30a, 30b and 30c, and terminates in the closed outer end 62.

Figure 2:
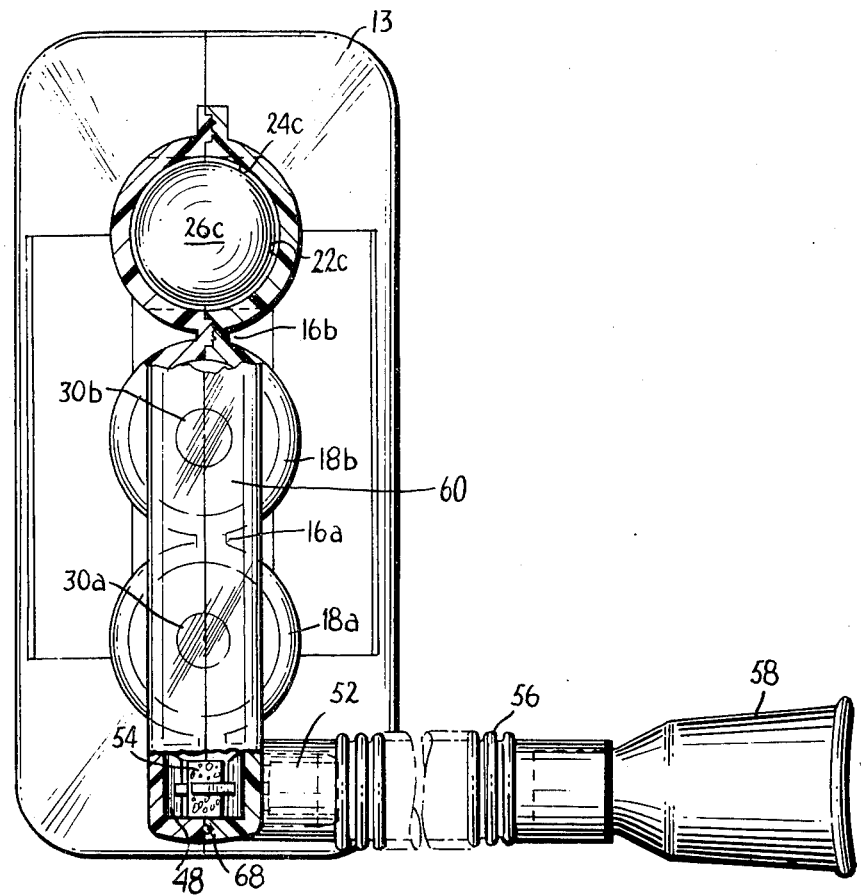
FIG. 2 is a plan view of the device illustrated in FIG. 1 with the top of the container broken away to show details in construction.
Figures 5, 6, 7:
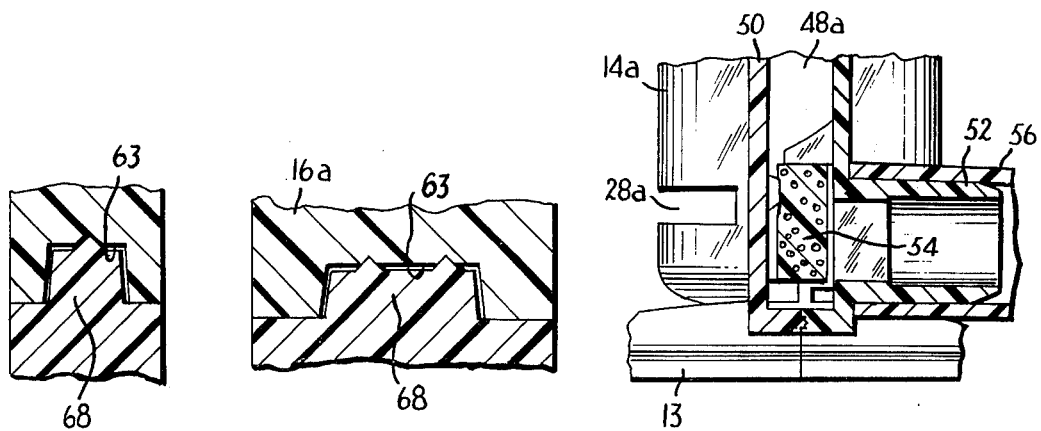
FIGS. 5 and 6 are sectional views of FIG. 4, taken along the line 5—5 and 6—6, illustrating the tongue and groove construction of the mating parts of the device.
FIG. 7 is a sectional view of FIG. 4, taken along lines 7—7, showing the filter in air passageway which prevents loose particles from being inhaled.

In the preferred embodiment illustrated in the drawings, the inspirator 10 is formed in a two part conventional injection mold. Each part is a vertical section of the inspirator, which, as illustrated in FIG. 2, is one-half of the assembled inspirator taken along its longitudinal center line. Also, as illustrated in FIGS. 2, 5 and 6, the face of the rear section is formed with tongues 62 in the outer channel and container walls and the intermediates interconnecting webs 16a and 16b. Correspondingly, the front section is formed with grooves 68 in the correspondingly front wall sections which slidably fit into the grooves 62.

In assembling the illustrated inspirator 10, the filter 54 is inserted in the outlet 52, balls 26a, 26b and 26c are placed in one section of the container 12 and the molded sections are brought together so as to cause the tongues 68 to fit into the grooves 62. With the inspirator 10 so assembled, the sections are ultrasonically welded together to form a single integral device 10. In doing so, the need for glue, the deleterious vapors of which remain long after use, is obviated.

In operation, the patient or user places his or her mouth over the mouthpiece 58 and inhales. This action causes air to be initially withdrawn from the air passageway 48 and chambers 24a, 24b and 24c. Because the first chamber 24a is closest to the point of inhalation, air flow through 28a into chamber 24a initially will be greater than in the other chambers 24b and 24c. Accordingly, inhalation at a precalibrated rate will cause the air flow into chamber 24a to first lift the ball 26a to the top of the chamber where it will close port 30a. Sustained inhalation at the precalibrated rate will cause the next ball 26b in the chamber 24b to rise and close port 30b. Finally, ball 26c in the last chamber 24c will rise to the top and come into contact with depending ridge 40 without abruptly disrupting air flow. The balls 26a, 26b and 26c will remain at the top of the chambers 24a, 24b and 24c as long as the user continues to expend a sufficient inhalation effort.

The device of the present invention therefore measures the minimum flow rate of inspiration needed to lift and maintain the balls 26a, 26b and 26c at the top of the container 12. In the device illustrated in the drawings, each ball 26a, 26b and 26c is about 1.0 inches in cross-section and weighs 1.5 grams, and each chamber 24a, 24b and 24c is about 4.70 inches in height and about 1.040 inches in cross-section. To raise the balls 26a, 26b and 26c in their respective chambers 24a, 24b and 24c, the user must inspire 1000 cubic centimeters per second of air. Thus, to raise the ball 26a the user must inspire still another 1000 cc per second. To sequentially raise all three balls to the tops of their chambers, the user must inspire at least 3000 centimeters in three seconds. For convenience the foregoing information may be imprinted directly on the base 13 or a label affixed to the base 13.

The action of the balls 26a, 26b and 26c is seen clearly because the air passageway 48 is alongside and on top of the container 12 giving the user an unimpeded view.

Further, the device of the invention is compact and easy to handle. The illustrated device stands some 6 inches high and is about 6 inches in length and is about three inches wide. Patients, therefore, easily can handle and operate the device. Flexible tubing 56 of some 11.0 inches has been found desirable and convenient to use.

In the illustrated embodiment, moreover, the filter 54 is made from urethane foam of about 0.620 inches in length and 0.370 inches in height and 0.187 inches in thickness. The illustrated filter 54 has 10 pores per inch and presents a tortuous path for air flow so that loose particles are prevented from passing therethrough.

The device 10 of the invention is preferably formed from plastics which are inert and stable in the formed device 10 and which lend themselves to processing by plastic forming techniques, and will, when formed, provide the see-through, self-supporting device described and claimed herein. In the preferred embodiment the device is formed by injection molding polystyrene. Other materials and plastics which provide the described properties also can be used, including styrene-acrylonitrile copolymers, rigid polyvinylchloride polymers and polycarbonate polymers.

Moreover, the flow rate of 1000 cubic centimeters per second for the device 10 illustrated in the drawings corresponds to a full deep breath. It is within the scope of this invention to provide devices which have flow rates that correspond to the condition of the patient. For example, by providing a smaller gap between each ball 26 and inner cylindrical wall 22, flow rates of 500 or 750 cubic centimeters per second per chamber are required to sequentially raise the balls. In another embodiment the flow rate could be graduated requiring a greater inhalation effort to raise the ball 26a in the first chamber 24a, then in the subsequent chambers 24b and 24c.

Figure 8:
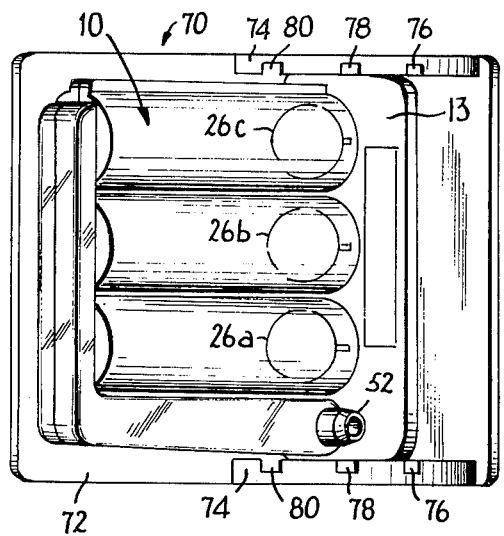
FIG. 8 is a plan view of the platform for maintaining the container at predetermined angles.

In addition, the device 10 can be titled to reduce the inhalation effort needed to raise and maintain each ball 26a, 26b and 26c at the top of the container 10. In the device 10 shown in the drawings by tilting the device 10 rearwardly, the lifting force needed to overcome the force of gravity is reduced. The greater the tilt the less the inhalation effort needed to achieve lifting and maintaining the ball at the top of the container 12. In tilting the device 10, however, it becomes more difficult to measure flow rate when the angle of tilt cannot be ascertained. To overcome this difficulty, the present invention includes, as shown in FIGS. 7 and 8, a platform 70 having a self-standing base 72 and two side walls 74. Included in each side wall are grooves 76, 78 and 80 which are set at 45°, 65° and 85° to the base 72. In use, base 13 of the container 12 is slidable into opposing grooves so that any one readily can tell the angle of the tilt.

The device 10 illustrated in the drawings is precalibrated to provide a flow rate for each chamber of 750 cubic centimeters per second at 45°; 650 cubic centimeters per second for each chamber at 65°; and 250 cubic centimeters per second for each chamber at 85°.

Thus, regardless of the condition of the patient, the present invention provides an incentive for a patient to use his or her lungs and chest. As that patient recovers, the angle of the tilt can be reduced until the device is vertically upright. In this way, the patient realizes his or her improvement.

Incentive levels also can be achieved by providing the devices of the invention with different numbers of chambers 24. For example, a two chambered device of the invention can be used when respiratory exercises are initiated and a four chambered device substituted when the patient is well on the way to a recovery.

Figure 9:
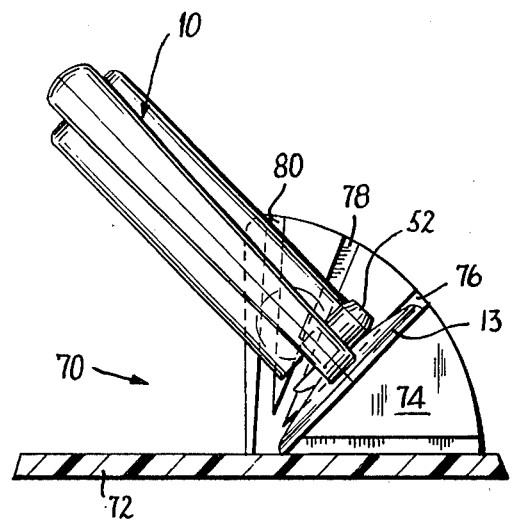
FIG. 9 is a side view of the platform with the foreground side wall removed to more clearly show the grooves into which the base of the device is slidable.
Figure 10:
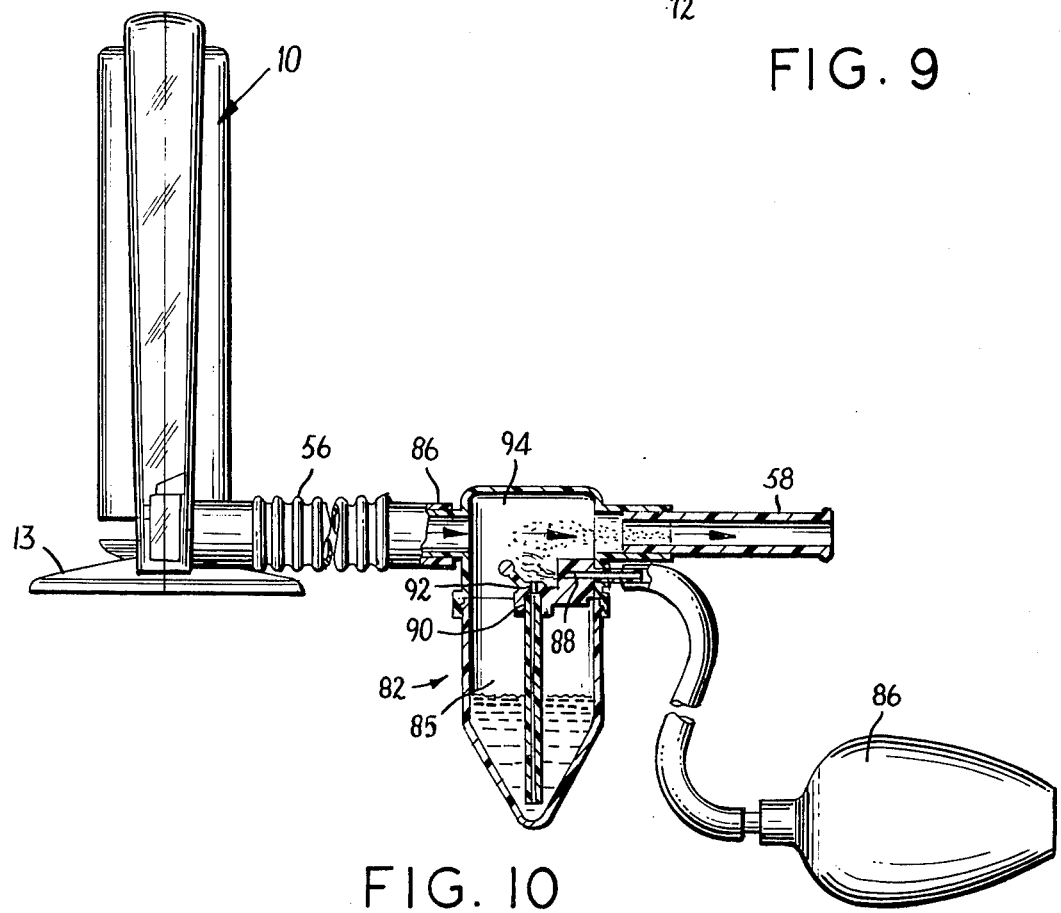
FIG. 10 is a side view, partly broken away, to show the dispenser for dispensing medicine through the flexible tubing upon inhalation.

As shown in FIG. 9, the present invention further includes a medicinal dispenser 82 connected at one end 84 to the mouthpiece 58 and at the other end 86 to the flexible tubing 56. Upon inhalation the patient will inspire the medicine in spray or powder form as he or she exercises his or her lungs and musculature. The medicinal dispenser 82 of the invention can be used to dispense bronchial dilators, water vapor, anti-inflammatory agents and asthmatic and other medicines. The reservoir 84 is filled with medication usually around 5cc. The patient inhales trying to raise the balls 26a, 26b and 26c. While inhaling, he squeezes on the bulb 86. Air from the bulb 86 is forced through the nozzle 88 and across the tip of the tube 90. This rapidly-forced air creates an upward venturi suction in the tube 90 thus lifting up medication from the reservoir 84. As medication squirts out the tube 90, the rapidly-forced air breaks up the liquid into an aerosol mist. The aerosol is further atomized by the diffuser 92 into smaller particles. Atomized medication is now is the upper mist chamber 94. Inhaled patient air rushes across the mist chamber thus carrying the atomized medication into the respiratory system of the patient. Large, unwanted particles fall back down into the reservoir. Only the desired small 0.5 micron or 6 micron particles are inhaled to reach deep into the lungs. The amount of medication delivered is controlled by viewing through the reservoir.

The invention in its broader aspect is not limited to the specific described embodiments and departures may be made therefrom within the scope of the accompanying claims without departing from the principals of the invention and without sacrificing its chief advantages.

What is claimed is:

1. A self-supporting incentive inhalation device for inducing respiratory exercise, comprising:
   a container having a plurality of transparent compartments in alignment along an axis of said container,
   said compartments each having a top wall, a bottom wall, a vertical wall therebetween, and a chamber therewithin which extends from said bottom wall to said top wall,
   a light-weight article in each of said chambers which is normally in the lower portions thereof,
   a slot in each of said compartments which extends through the lower portion thereof and connects each of said chambers to the surrounding atmosphere at a point at least partially below each of said articles,
   a passageway in said container which extends over said compartment top walls and has an outlet adjacent one of the outer of said chambers,
   a restricted port in each compartment which extends through said top wall thereof and connects said chambers to said passageway,
   a ridge in said last compartment depending from the top wall thereof to prevent said article therein from closing said last top port,
   means connected to said outlet to allow a person to withdraw air from said chambers through said passageway, whereupon said article is said chamber adjacent said outlet rises to the top thereof and closes said top port when a person inspires air at a precalibrated flow rate, said article in each intermediate chamber sequentially rises to the top thereof and closes each intermediate top port when a person inspires predetermined additional amounts of air at a precalibrated flow rate, and said article in the last of said chamber rises to the top thereof and contacts said depending ridge therein when a person inspires still an additional predetermined amount of air at a precalibrated flow rate.

2. The inhalation device according to claim 1, wherein
   said container has three compartments with three vertical chambers aligned along the longitudinal axis of the device,
   said passageway outlet is adjacent to the first chamber, and
   said last said means is tubing connected at one end to said outlet and at its other end to a mouthpiece.

3. The inhalation device according to claim 2 in which said passageway is within a channel which extends over said top walls and alongside said first compartment where said channel is connected to said passageway outlet.

4. The inhalation device according to claim 2, wherein said container is mounted on a base upon which the device stands in an upright position.

5. The inhalation device according to claim 2, wherein said articles are light-weight balls.

6. The inhalation device of claim 2 in which a medicinal dispenser is connected between said outlet and said tubing for dispensing medicine upon inhalation.

7. The inhalation device of claim 1 in which said precalibrated flow rate is about 1000 cubic centimeters per second.

8. The inhalation device of claim 1 in which the device is made of polystyrene and is formed from a plurality of pieces ultrasonically welded together into a single, integral unit.

9. The inhalation device of claim 1 in which said device includes means for maintaining said container at a predetermined angle to reduce the flow rate necessary to cause said articles to rise and be maintained at the top of said container.

10. The inhalation device of claim 9 in which said device includes a platform into which said container is slidable at predetermined acute angles to reduce the flow rate necessary to cause said articles to rise and be maintained at the top of said container.

11. An incentive inhalation device for inducing respiratory exercise, comprising:
    a container having a plurality of see-through compartments therein, in each of which is a chamber,
    flow rate indicator means in each chamber which normally rests in the lower portion thereof and having a clearance between each indicator means and its chamber wall which allows free movement of the indicator means but restricts air flow thereabout to cause said indicator means to rise towards the top of its chamber when the inhalation effort by a patient reaches a precalibrated rate of air flow,
    an opening in the lower portion of each chamber connecting the chamber, to the surrounding atmosphere for lifting the flow indicator means therein,
    an opening in the top portion of each chamber,
    a passageway connected to each chamber through said opening in the top portion of each chamber, and
    outlet means connected to said passageway to allow a person to withdraw air from each chamber and to cause air to be drawn into each chamber through said opening therein for lifting said flow indicator means to the top of each chamber when the inhalation effort is at least the precalibrated rate of air flow for each chamber.

12. The inhalation device according to claim 11, wherein said chambers are adjacent one another and vertical when the device is in an upright position, and said outlet means has an outlet connected to said passageway adjacent one of said chambers.

13. The inhalation device according to claim 11, wherein each of said lower openings extends through the front and back of each of said vertical chambers at a point at least partially below each of said indicators.

14. The inhalation device according to claim 13, wherein a port extends through the top of each compartment for connecting each of said chambers to said passageway, and said passageway extends over the top of each compartment to said outlet.

15. The inhalation device according to claim 14, wherein means are provided in the last of said chambers which prevents said article therein from closing the last of said top ports.

* * * * *

UNITED STATES PATENT AND TRADEMARK OFFICE
CERTIFICATE OF CORRECTION

PATENT NO. : 4,060,074
DATED : November 29, 1977
INVENTOR(S) : Ronald D. Russo

It is certified that error appears in the above-identified patent and that said Letters Patent are hereby corrected as shown below:

Column 1, line 57, After "indicator" correct "for" to read --but--.

Column 3, line 51, After "which" correct "from" to read --form--.

Column 6, line 18, Correct "titled" to read --tilted--.

Column 7, line 9, Before "6" correct "or" to read --to--.

Signed and Sealed this

Sixteenth Day of May 1978

[SEAL]

Attest:

RUTH C. MASON
Attesting Officer

LUTRELLE F. PARKER
Acting Commissioner of Patents and Trademarks